United States Patent [19]

Vailancourt

[11] Patent Number: 4,512,766
[45] Date of Patent: Apr. 23, 1985

[54] CATHETER VALVE

[75] Inventor: Vincent L. Vailancourt, Livingston, N.J.

[73] Assignee: Whitman Medical Corporation, Clark, N.J.

[21] Appl. No.: 447,935

[22] Filed: Dec. 8, 1982

[51] Int. Cl.[3] .......................... A61M 5/00; A61B 5/00
[52] U.S. Cl. ................................... 604/169; 128/764; 604/256
[58] Field of Search ............... 128/763, 764; 604/167, 604/169, 236, 237, 247, 256

[56] References Cited

U.S. PATENT DOCUMENTS

| 3,097,646 | 7/1963 | Scislowicz | 604/167 |
| 3,853,127 | 12/1974 | Spademan | 604/167 |
| 4,261,357 | 4/1981 | Kontos | 604/167 |
| 4,444,203 | 4/1984 | Engelman | 128/764 |

FOREIGN PATENT DOCUMENTS

| 2903167 | 7/1980 | Fed. Rep. of Germany | 128/764 |
| 272034 | 2/1930 | Italy | 128/764 |
| 1199498 | 7/1970 | United Kingdom | 604/256 |

Primary Examiner—Dalton L. Truluck
Attorney, Agent, or Firm—Holman & Stern

[57] ABSTRACT

An intravenous catheter assembly includes a valve located in the catheter hub and made of needle-penetrable self-sealing material such as rubber. The valve is biased to a closed position wherein it surrounds an inlet end of a hollow elongated insert disposed in the hub. The insert is in flow communication with a catheter tube and serves as an outer sleeve for an insertion needle which is inserted through a puncture in the valve to pass through the insert and catheter tube. Upon removal of the needle the valve puncture self-seals. The valve is larger than the flow passage opening of a standard Luer tapered male fitting which, when inserted into the hub, axially translates the valve along the insert until the insert projects through the valve puncture and into the Luer male fitting flow passage. The positional bias for the valve is provided by a helical spring disposed about the insert by extending an integral part of the valve as an axially compressible resilient sleeve surrounding the insert.

17 Claims, 5 Drawing Figures

CATHETER VALVE

BACKGROUND OF THE INVENTION

1. Technical Field

The present invention relates to intravenous catheter assemblies and, more particularly, to an improved valve for use in such assemblies.

2. Prior Art

Intravenous catheters, through which medication is delivered, are subject to the danger of air embolism and uncontrolled hemorrhaging. For example, this danger exists in such procedures as cardiac catheterization, central venous catheterization for parenteral nutrition, arterial catheterization, intravenous therapy, etc. Air embolism and uncontrolled hemorrhaging can occur during catheter insertion, removal of the insertion needle, removal of the syringe for purposes of threading the catheter or tube changes, and also, if the intravenous tubing connector is inadvertently detached from the catheter, particularly by the patient.

Attempts to solve the problem of inadvertent separation of the catheter tubing and connector have included taping the components together or physically forcing the components into one another; however, these attempts have not solved the problem.

After insertion of the catheter, it is standard practice to apply digital pressure to the catheter lumen to pinch off the catheter tube from the time the needle is withdrawn until connection of the hub to the intravenous or other administration set. Unless this is done properly, blood from the catheter tube exits through the catheter hub and, more importantly, compromises sterility of the fluid path. In the case of arterial punctures, the blood may even squirt into the air and across the room. In addition, there is a concern that pressing the catheter lumen at the puncture site may, of itself, compromise sterility. Specifically, the catheter, after being connected to the administration set, is inserted further into the blood vessel and the site where digital pressure was applied may be positioned within the blood vessel.

It will also be appreciated that the requirement to apply digital pressure to the catheter tube fully utilizes one hand of the practitioner, leaving only the other hand to make necessary manipulations, such as removing the needle, applying the Luer adaptor of the administration set to the catheter hub, etc. In practice, the practitioner applies digital pressure using the middle finger of the left hand and grabs the hub with the thumb and forefinger of that hand. The Luer adaptor of the administration set is secured with the right hand and the two parts are brought together. Should any complication ensue, the middle finger, which applies the digital pressure, is moved and blood flows out through the catheter.

In attempts to overcome the afore-mentioned problems, so-called side arm catheters, such as those described in U.S. Pat. No. 3,853,127 to Spademan and U.S. Pat. No. 4,310,017 to Raines, have been proposed. Although such catheters do overcome the aforesaid problem, they are somewhat complex, bulky at the insertion site and do not provide any protection in the event that the intravenous tubing connector becomes disconnected from the hub.

Other attempts to overcome the problem of sterile bloodless venipuncture are found in U.S. Pat. Nos. 4,245,635 and 4,261,357 to Kontos. The catheter assemblies in these Kontos patents employ floating check valves which, in theory, solve the problem described above. However, such valve arrangements require that the insertion needle be bent while it is in the catheter assembly, thereby increasing the likelihood of needle breakage. Moreover, the open position of the valve in these devices is such that it provides some restriction to flow from the administration set adaptor to the catheter tube. Moreover, the floating check valve embodiment is not readily adaptable to standard-type catheter assemblies presently on the market.

OBJECTS AND SUMMARY OF THE INVENTION

It is a primary object of the present invention to provide a catheter assembly accomplishing bloodless puncture of veins and arteries, wherein blood is automatically prevented from exiting from the catheter hub between the time the needle is removed and the medication administration set is attached.

It is a further object of the present to eliminate the need for applying digital pressure to the catheter lumen after the insertion needle of a catheter assembly is removed and before the intravenous administration set is attached.

It is another object of the present invention to eliminate compromise of sterile technique during catheter insertion while preventing loss of blood.

It is a further object of the present invention to provide a safety valve which precludes air from entering the blood circulatory system when a line is inadvertently disconnected from the catheter assembly.

Still another object of the present invention is to provide an inexpensive and easily fabricated valve which adds no bulk to a catheter assembly at the insertion site.

A still further object of the present invention is to provide an intravenous catheter assembly valve which is adaptable for use in most, if not all, of the standard catheter assemblies presently available.

In accordance with the present invention a standard catheter hub is internally fitted with an elongated hollow insert which is preferably made of stainless steel. A flange extends radially from the insert and, in one embodiment, secures the insert to the catheter hub, utilizing an interference fit. The opposite end of the insert is open and terminates in a sharpened annular edge. An elastomeric valve member is placed over the open insert end and, in one embodiment, is an elongated tube or sleeve having a closed valving end which is sealed. The elastomeric valve is made of a self-sealing material so that it can be punctured by a needle and then sealed automatically when the needle is removed. The open end of the valve member engages the side wall of the catheter hub or the insert flange and seals off the insert inlet end from the entrance to the catheter hub. The closed end provides an engaging surface for a male Luer adaptor such that when the adaptor is positioned within the catheter hub it forces the elastomeric tube to slide longitudinally along the insert and past the insert inlet. As the elastomeric tube moves, a puncture or slit, previously placed in the wall of the closed end of the elastomeric tube, expands over the insert inlet as the tube compresses axially. The insert inlet projects into the male Luer adaptor, creating a port or entrance between the adaptor and catheter lumen through which fluid may pass. When the adaptor is removed, the compressed elastomeric member expands and closes the insert. Clearance is provided between the elastomeric member and both the insert wall and hub wall to permit the valve to compress axially. This clearance also permits rapid closure of the valve when the male Luer adaptor is removed. When a needle is used to make the blood vessel puncture through the catheter assembly, the needle passes through the slit in the elastomeric valve member, but does not force the elastomeric member to ride up over the insert. Therefore, when the needle is removed, valve closure is substantially instantanous. More importantly, the valve member is not subjected to elongation over the insert during sterilization which, as is well known, causes a permanent deformation with loss of sealing properties.

In another embodiment of the invention, valve member surrounds only the insert inlet portion and is biased closed by a helical spring disposed about the insert.

BRIEF DESCRIPTION OF THE DRAWINGS

The above and still further objects, features and advantages of the present invention will become apparent upon consideration of the following detailed description of the specific embodiments thereof, especially when taken in conjunction with the accompanying drawings, wherein.

FURTHER DESCRIPTION OF PREFERRED EMBODIMENTS

Figure 1:
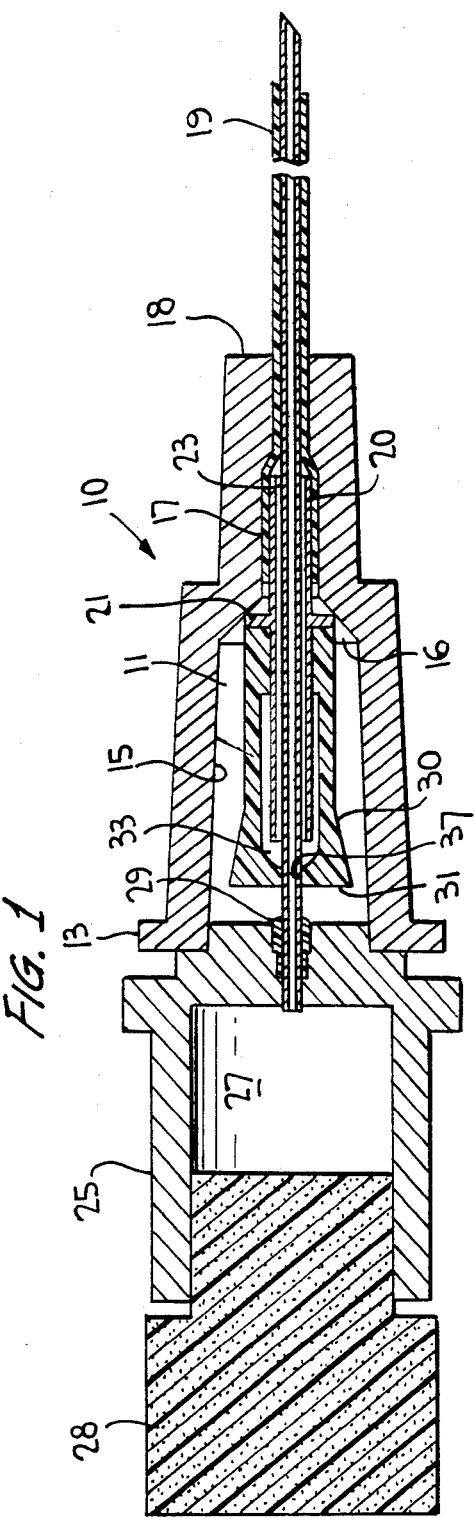
FIG. 1 is a view in section, partially broken, of a catheter assembly of the present invention with a needle and needle holder unit inserted into the catheter hub.

Referring specifically to FIG. 1 of the accompanying drawing, an intravenous catheter assembly includes a catheter hub 10 which is open at one end to provide access to an interior hub chamber 11. The open hub end is surrounded by an annular flange 13 which extends radially outward to facilitate gripping of the hub during removal of a needle unit and during insertion and removal of a connector for a medicament administration set. Chamber 11 is generally frusto-conical and is peripherally bounded by a wall 15 which slowly tapers in a direction away from the open end, preferably in accordance with the ANSI Z70.1 performance standard for medical Luer taper fittings. The end section 16 of chamber 11, remote from the open end, tapers more sharply and terminates in a bore 17 which extends from chamber section 16 all the way to the distal end 18 of hub 10 remote from flange 13.

A catheter tube or lumen 19 has one end secured in bore 17 and a remote end which projects through the distal end 18 of the hub for insertion into a blood vessel. The hollow cylindrical catheter tube 19 is conventional in all respects and has an internal cylindrical bore which is sufficiently large to conduct liquid medicament flow into a vascular puncture. An insertion member 20, in the form of an elongated hollow flow tube, extends from the hub chamber 11 into bore 17 and concentrically within the proximal end of catheter tube 19. The flow insert 20 secures the catheter tube in bore 17 with a tight interference fit to prevent inadvertent longitudinal and rotational displacement of the catheter tube and its removal from the hub. In this regard, the section of bore 17 closest to chamber 16 may have a somewhat larger diameter than the rest of the bore (as shown in FIG. 1) to properly receive the radially-expanded end of catheter tube 19 in which the insert member 20 is disposed.

Insert member 20 has an annular flange 21 extending radially outward from a location intermediate the ends of the insert. The diameter of flange 21 is such that the insert member can be engaged in chamber section 16 in a friction or interference fit. The portion of insert member 20 which extends into chamber 11 is sufficiently long to be partially inserted into a standard male Luer adaptor which is received in the hub chamber in the manner described below in relation to FIG. 2. Insert member 20 is preferably made of stainless steel but can be made of plastic material if desired. The hub is conventionally made of either plastic material or metal. The catheter tube is preferably and conventionally made of a plastic material, such as Teflon, having a low-friction outer surface.

Figure 2:
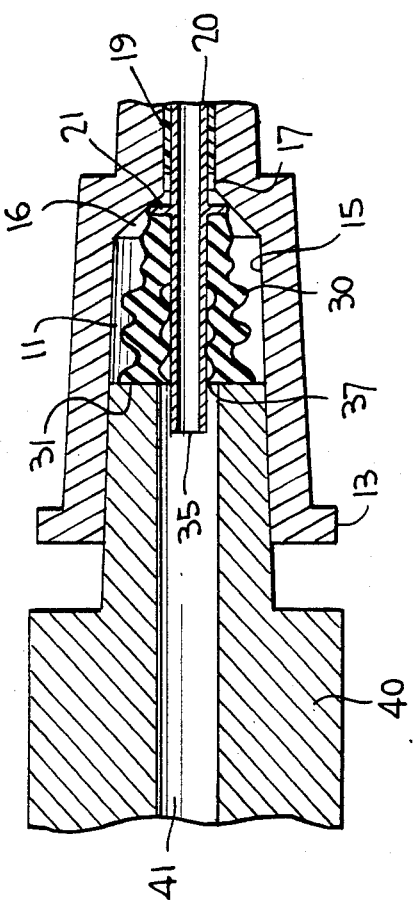
FIG. 2 is a view in section of a portion of the catheter assembly of FIG. 1 shown with a male Luer adaptor inserted into the catheter hub.

Catheter tube 19 and insert member 20 constitute a flow passage for administering medicament to a patient in the manner to be described in relation to FIG. 2. In addition, the catheter tube and insert member serve as a guide for a needle 23 employed with the catheter assembly to effect a puncture in a blood vessel prior to insertion of the catheter tube 19 into that blood vessel. Specifically, the needle 23 extends from a conventional needle holder 25 which has a transparent flashback chamber 27. The proximal end of the needle 23 is open to the flashback chamber and the needle itself is secured by epoxy 29, or the like, in an aperture at the forward end of the needle holder 25. That forward end of needle holder 25 is shown partially in hub chamber 11 and partially abutting hub flange 13, in which position the needle 23 extends through insert member 20 and catheter tube 19 to project beyond the distal end of the catheter tube. The rearward end of the needle holder 25 is fitted with an air-porous plug 28 which closes the flashback chamber. The porosity of plug 28 permits vent air to escape from the flashback chamber so that blood can enter, but prevents blood from flowing through the plug.

The structure as thus far described, with the exception of the length of insert member 20 which extends into chamber 11 from flange 21, is conventional and corresponds to catheter assemblies which are presently commercially available. Such assemblies are generally sold with the needle and needle holder assembled with the hub as illustrated in FIG. 1. In accordance with the present invention, the conventional catheter assembly is modified by extending insert member 20 into the hub chamber 11 and providing a hollow elastomeric valve member 30 in the hub chamber. Valve member 30 is made of rubber or a suitable material such as styrene-butadiene copolymer. It must be pierceable by needle 23 through a puncture or slit 37 made by the needle, or pre-existing in the valve, and it must be re-sealable upon removal of the needle. The embodiment of the valve member 30 illustrated in FIG. 1 has a flat circular near end 31 which faces the open end of hub 10. The diameter of valve end 31 is smaller than the diameter of the adjacent wall 15 of hub chamber 11 so that an empty annular space 33 exists between the valve and 31 and the chamber wall. The exterior or the valve member 30 tapers slightly for a short forward distance from valve end 31 and remains a constant diameter cylinder throughout most of its length. This latter diameter is preferably equal to or slightly less than the outer diameter of the flange 21 of insert member 20. The interior of valve member 30 includes a relatively large diameter section 33 disposed about and spaced from the proximal or inlet end of insert member 20. It is to be noted that the spacing of the valve member from the insert member within section 33 includes both radial spacing along a portion of the insert member length and axial spacing from annular edge 35 of the inlet end of the insert member. The other end of the valve member interior surrounds and contacts the insert member periphery. The remote end of valve member 30 abuts flange 21 which acts as a stop against longitudinal displacement of the valve member toward the distal end of the hub.

As illustrated in FIG. 1, when needle 23 is in place in the catheter assembly, the needle extends through a puncture or slit 37 in the near end 31 of the valve and from there passes through insert 20 and cathether tube 19. Puncture 37 may be made by needle 23 when the needle is initially inserted into the assembly. Alternatively, the puncture may be a slit which is pre-formed in the valve member. In either case, the resilient valve material is such that the puncture or slit 37 automatically re-seals itself against fluid flow therethrough when the needle is removed.

With specific reference to FIG. 2, after needle 23 has been removed from the hub, a male Luer adaptor 40 from an administration set may be inserted into chamber 11. The forward end of adaptor 40 peripherally tapers to match the wall 15 of hub chamber 11 to provide a friction or interference fit engagement after the male adaptor has been sufficiently inserted into the chamber. Such interference fit engagement with Luer fittings are conventional and are constructed in accordance with the aforesaid ANSI Z70.1 specification. Adaptor 40 has a central longitudinally-extending bore 41 which serves as a supply passage for medicament fluid from an administration set. The diameter of bore 41 is greater than the diameter of the annular inlet edge 35 of insert member 20 but is smaller than the diameter of near end 31 of the valve member. In addition, the insertion depth required of the adaptor 40 in chamber 11 before an interference fit engagement is achieved is greater than the spacing of inlet edge 35 of insert member 20 from the open end of the hub chamber. These dimensional features result in the forward end of adapter 40 forcing the valve member 30 to compress axially about insert member 20 when the adaptor is fully inserted in hub member 11. Specifically, the forward end of the adaptor abuts near end 31 of the valve member 30 and translates it axially past the edge 35 of insert member 20, thereby causing the valve member to buckle or collapse axially against the resilient bias which continously urges the valve member 30 to its extended or closed position illustrated in FIG. 1. In the collapsed or open valve position, illustrated in FIG. 2, inlet edge 35 of insert member 20 projects through the valve and into the bore or passage 41 of the male adapter 40. A flow path is thus provided from the passage 41 through the catheter tube 19 via insert 20. For this purpose, annular edge 35 may be sharpened by tapering its wall thickness to facilitate passage through the puncture or slit 37.

In operation, with needle 23 inserted through the valve 30 (as illustrated in FIG. 1), insert member 20 and catheter tube 19, a puncture is made in an artery or vein with the distal end of needle 23. Since valve 30 is closed, the only flow path through the hub chamber 11 is through needle 23 which conducts blood from the puncture site to flashback chamber 27. When blood is observed in the flashback chamber, the catheter tube is inserted into the punctured blood vessel to the extent required by the procedure. The practitioner then removes the needle by grasping hub 10 with one hand and pulling the needle holder 25 backward with the other hand. Since the valve 30 is not compressed throughout this insertion procedure, the valve remains closed and prevents air from entering the puncture site via the catheter tube while blocking blood flow out of the interior space 33 of the valve member. It is to be noted that both hands are free to grasp the hub and needle holder because the valve 30 eliminates the need to apply digital pressure to the catheter tube to prevent bleeding and air embolism. The male Luer adapter 40 may then be inserted, as illustrated in FIG. 2, until the valve 30 is opened and the insert member 20 extends into bore 41. Medicament flow can then be initiated. The adaptor 40 can be removed and re-inserted or replaced with another adaptor without danger of hemorrhaging or air embolism. It should further be noted that the valving is achieved without compromising the sterile technique at any point in the procedure.

The annular spaces between the valve 30 and both chamber wall 15 and insert member 20 facilitate axial collapse of the valve member at the urging of the inserted adapter 40 against a natural extension bias of the valve. The axial collapse can be further facilitated by placing a few drops of silicone in the interior region 33 of the valve.

The important aspect of the invention is the relationship between the valve member 30, insert member 20 and adapter 40 in hub chamber 11 which permits the insert member to project into the adapter bore 41 in the open valve position. In addition, the valve and the insert permit needle 23 to pass therethrough so as to conduct blood to the flashback chamber without opening the valve and without compromising the sterile technique.

It can be seen that the valving arrangement, requiring only valve member 30 and modified insert member 20, is inexpensive to fabricate and is easily adapted to existing catheter assemblies.

Figure 3:
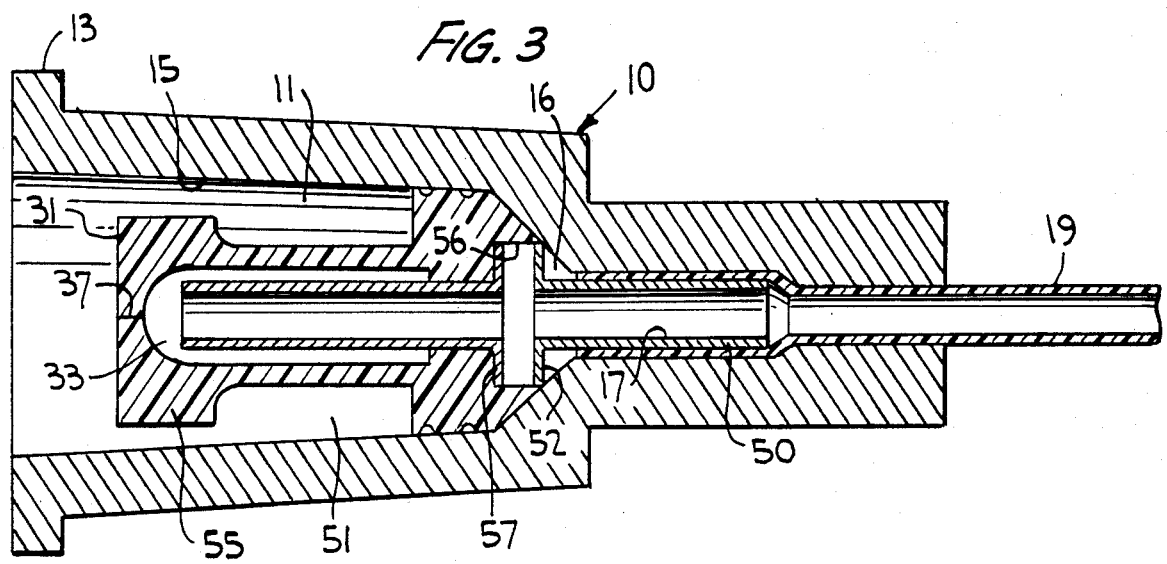
FIG. 3 is a view in section of a second catheter hub assembly embodiment of the present invention.

An alternative embodiment of the invention is illustrated in FIG. 3 wherein elements identical to those in the embodiments of FIGS. 1 and 2 bear the same reference numerals. In FIG. 3, instead of replacing the conventional insert member with a double-ended insert member 20, the conventional insert member 50 is retained and a second insert member 51 is employed. In addition, the valve member 30 is replaced with valve member 55 of somewhat different contour to permit the hub chamber wall to serve as the longitudinal stop rather than having the insert member flange serve this function. More specifically, conventional insert member 50 has an outwardly-extending annular flange 52 at one end, which flange engages the wall in chamber section 16 in an interference fit. The remainder of the insert member 50 is a cylindrical tube which extends into bore 17 and secures catheter tube 19 in place.

The support end of valve member 55 is enlarged and tapered at its extremity to abut and match the taper in chamber section 16. The outer periphery of the support end of valve member 55 contacts chamber wall 15 in a friction fit. The support end of the valve member 55 is therefore prevented from moving toward the distal end 18 of the hub 10 by the chamber wall. Axial collapse of this valve member, upon insertion of adapter 40, occurs along the relatively thin-walled section 54 existing between the thicker end of sections of the valve member.

An axially short annular recess 56 is centrally defined in the support end of the valve member 55. The diameter of annular recess 56 is substantially equal to the diameter of flange 52 of conventional insert 50 so that flange 52 resides right at the mouth of the recess. The additional insert 51 is configured similar to insert 50 and has an annular flange 57 which resides in recess 56. Flange 57 has a diameter equal to recess 56 and is axially spaced from flange 52 of insert 50. The stem or tubular portion of insert member 51 is slightly longer than that of insert member 50 and extends in the opposite direction into the interior space 33 of the valve member.

Operation of the embodiment of the valve in FIG. 3 is the same as that described in relation to FIGS. 1 and 2. Valve 55, in addition to providing a seal against the insert member, provides a seal along the hub chamber wall. It should be noted that the permanent contact between the valve member and the insert, in both embodiments described hereinabove, may be by interference fit, by adhesive connection, or both.

Figure 4:
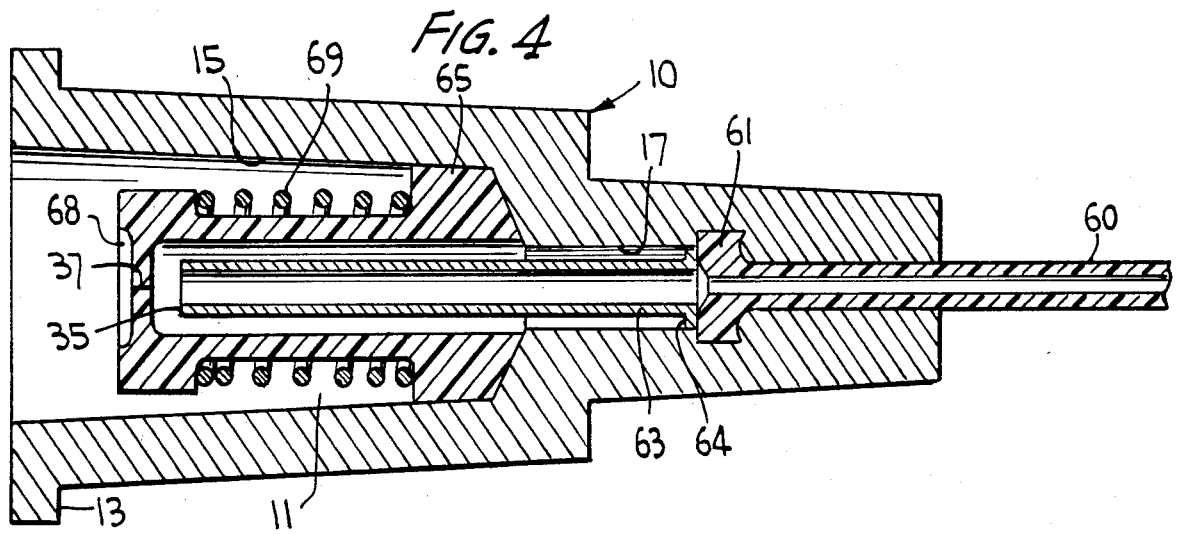
FIG. 4 is a view in section of a third catheter hub assembly embodiment of the present invention.

Referring specifically to FIG. 4 of the accompanying drawings, the valving arrangement of the present invention is shown adapted to another type of catheter assembly which is commercially available. Elements of this embodiment which are similar to those in FIGS. 1, 2 and 3 bear the same reference numerals. In the embodiment of FIG. 4, the catheter tube or lumen 60 has an annular flange 61 disposed in an axially short radially-enlarged section of bore 17. This short bore section is formed from an axially elongated bore section of similarly enlarged diameter extending to the distal end 18 of the hub. The catheter tube flange 61 is inserted fully into the bore section which is then filled around the catheter tube by any suitable method, such as heat forming to effect plastic flow, ultrasonic welding or insert molding. The plastic insert member 63 has a radially-extending annular flange 64 which abuts the catheter tube flange 61 such that the catheter tube and insert are oriented in coaxially-lined, end-to-end relationship. The flanges 61, 64 are secured to one another by heat forming, insert molding, etc. In this embodiment, the stem portion of the insert member 63 extends into the interior space 67 of the valve member 65 without contacting the valve member at any point along the length of the insert member. This is an optional feature since the valve member interior could readily be reduced at the support end of the valve to contact the insert member. Valve member 65 has its support end contoured to match the chamber section 16 and part of chamber wall 15. The engagement of the valve member 65 in the hub is achieved by interference fit and/or adhesive against these walls.

The valve inlet end is shown recessed at 68 in FIG. 4 to reduce its thickness and thereby facilitate penetration of slit or puncture 37 by the annular edge of insert member 63. This feature can also be employed in the other valve embodiments described herein.

In order to increase the speed of closing the valve member, a helical spring 69 may be provided about the valve member between its radially-enlarged ends. Spring 69 aids the natural resilient bias of the valve member to snap the valve back to its extended or closed position after the male Luer adapter is removed from the hub chamber. This spring assist feature can be employed in any of the embodiments described hereinabove. In addition, the valve concept of the present invention may employ only a spring bias, without using an axially resilient valve, and without axially compressing the valve member itself. Such an embodiment is illustrated in FIG. 5.

Figure 5:
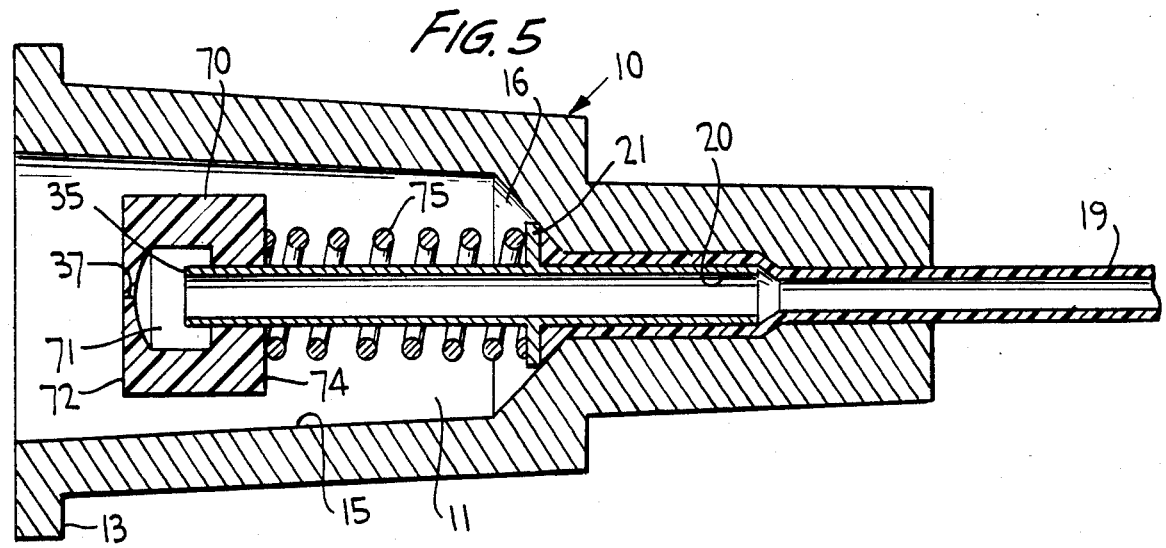
FIG. 5 is a view in section of a fourth catheter hub assembly embodiment of the present invention.

Referring specifically to FIG. 5, wherein elements similar to those in other figures bear the same reference numerals, the insert member 20 with intermediate flange 21 is provided. The valve member 70, instead of extending to the flange 21 or to the end section 16 of chamber 11, extends along only a short part of the length of the insert member 20 proximate annular edge 35. Valve member 70 takes the form of a cylinder having a circular near end surface 72 and an annular far end surface 74. A central longitudinally-extending bore is defined through far end surface 74 and communicates with the valve interior space 71. The inlet edge 35 of insert member 20 projects through this bore into the valve interior space 71. The bore fits slidably about a short length of the insert member forward of the edge 35 so as to slidably engage the insert member.

A helically coiled spring 75 is disposed concentrically about the insert member 20 in chamber 11 and extends between insert member flange 21 and far end surface 74 of the valve member 70. Spring 75 biases the valve member to the closed position shown in FIG. 5. When a male Luer adapter forces the valve member 70 axially along insert member 20, spring 75 is compressed to permit inlet edge 35 of the insert member to project through slit 37 and into the male Luer adapter.

While I have described and illustrated various specific embodiments of my invention, it will be clear that variations from the details of construction which are specifically illustrated and described may be resorted to without departing from the true spirit and scope of the invention as defined in the appended claims.

I claim:

1. An intravenous catheter assembly, comprising:
a catheter hub having first and second ends and an interior hub chamber which is opened at its first end and is perpherally bounded by a chamber wall;
elongated flow passage means having a near end disposed within said hub chamber and terminating in a remote end beyond said second end of said hub, said near end of said flow passage means being spaced from said chamber wall and having a first pre-determined cross-sectional configuration;
a valve member disposed in said hub chamber about said flow passage means at said near end of said flow passage means for blocking flow between said hub chamber and said near end of said flow passage means, said valve member being made of self-sealing resilient material which permits a needle to be inserted and then withdrawn from a puncture in said valve member from said open end of said hub chamber without destroying the flow blocking capability of said valve member, said valve member having a second pre-determined cross-sectional configuration which is larger than said first pre-determined cross-sectional configuration of said near end of said flow passage means in order to permit the valve member to be forced axially along the outside of said flow passage means with said near end extending through a puncture in said valve member;
bias means for urging said valve member axially toward said open end of said hub;

a needle and needle holding unit adapted to be inserted into said hub chamber from said open end with said needle extending through a puncture in said valve member and through said flow passage means to beyond the remote end of said flow passage means, said needle holding unit including a substantially transparent flashback chamber for receiving blood from said puncture via said needle; and adaptor means adapted to be inserted into said open end of said hub for delivering fluid through said flow passage means after said needle and needle holder unit has been removed, said adaptor means comprising a supply passage having a cross-sectional configuration which is larger than said first pre-determined cross-sectional configuration but smaller than said second pre-determined cross-sectional configuration, whereby forcing said supply passage over said near end of said flow passage means forces said valve member axially in opposition to said bias means along said flow passage means with the near end of said flow passage means projecting into said supply passage through the puncture in said valve member through which said needle had been extended.

2. The intravenous catheter assembly according to claim 1 wherein said bias means is an integral part of said valve member which is formed as a resilient sleeve surrounding a portion of said flow passage means and having a closed end disposed between the near end of said flow passage means and the open end of said hub.

3. The intravenous catheter assembly according to claim 2 wherein said resilient sleeve has an open end, and further comprising support means in said chamber for abutting and limiting axial displacement of said open end of said resilient sleeve to permit axial compression of said sleeve about said flow passage means in response to forcing of said supply passage over said flow passage means.

4. The intravenous catheter assembly according to claim 3 wherein said support means includes a wall of said chamber.

5. The intravenous catheter assembly according to claim 3 wherein said hub chamber has a downstream end remote from said open end of said hub and has a downstream end wall which converges in a direction away from said open end of said hub, and wherein the open end of said resilient sleeve is tapered to match and abut said downstream end wall, wherein said support means comprises the abutment of said downstream end wall and the open end of said resilient sleeve.

6. The intravenous catheter assembly according to claim 3 wherein said flow passage means includes a shoulder portion extending outwardly therefrom, wherein the open end of said resilient sleeve abuts shoulder portion to comprise said support means.

7. The intravenous catheter assembly according to claim 1 wherein said bias means comprises spring means disposed in said chamber for resiliently urging said valve member towards said open end of said hub.

8. The intravenous catheter assembly according to claim 7 wherein said spring means comprises a helical spring disposed about said flow passage means.

9. The intravenous catheter assembly according to claim 1 wherein said flow passage means comprises:

a catheter tube having a proximal end which extends from said hub to a remote vascular insertion end;

an elongated hollow insert having a distal end secured to and in flow communication with the proximal end of said catheter tube, an upstream end which is disposed in said chamber such that flow communication between the chamber and said upstream end of said insert is controlled by said valve member, said upstream end of said insert corresponding to the near end of said flow passage means.

10. The intravenous catheter valve assembly according to claim 9 wherein said valve member is a resilient sleeve disposed about said insert at said upstream end and having a closed end disposed between said open end of said hub and said upstream end of said insert.

11. The intravenous catheter assembly according to claim 10 wherein said resilient sleeve has an open end, and further comprising support means in said chamber for abutting and limiting axial displacement of said open end of said resilient sleeve to permit axial compression of said sleeve about said insert in response to forcing of said supply passage over said insert.

12. The intravenous catheter assembly according to claim 11 wherein said insert is an elongated hollow tube having a generally radially-extending shoulder which abuts the open end of said sleeve and corresponds to said support means.

13. The intravenous catheter assembly according to claim 12 wherein said resilient sleeve is radially spaced from said insert over at least a part of the length of said insert which includes said upstream end.

14. The intravenous catheter assembly according to claim 13 wherein said shoulder is disposed intermediate the extreme ends of said insert.

15. The intravenous catheter assembly according to claim 13 wherein said shoulder is disposed at the distal end of said insert.

16. The intravenous catheter assembly according to claim 15 further including a further elongated hollow insert disposed in axial alignment with the first-mentioned insert and secured to said catheter tube.

17. The intravenous catheter assembly according to claim 13 wherein said hub chamber has a downstream end remote from said open end of said hub and which has a downstream end wall which converges in a direction away from said open end of said hub and wherein the open end of said resilient sleeve is tapered to match and abut said downstream end wall, wherein said support means comprises the abutment of said downstream end wall and the open end of said resilient sleeve.

* * * * *